(12) United States Patent
Reynolds et al.

(10) Patent No.: US 7,338,761 B2
(45) Date of Patent: Mar. 4, 2008

(54) DETECTION AND QUANTIFICATION OF HUMAN HERPES VIRUSES

(75) Inventors: Thomas R. Reynolds, Midlothian, VA (US); Robert B. Harris, Midlothian, VA (US)

(73) Assignee: Vigen Laboratories Inc., Wilmette, IL (US)

( * ) Notice: Subject to any disclaimer, the term of this patent is extended or adjusted under 35 U.S.C. 154(b) by 423 days.

(21) Appl. No.: 10/399,872

(22) PCT Filed: Oct. 12, 2001

(86) PCT No.: PCT/US01/31892

§ 371 (c)(1),
(2), (4) Date: Sep. 8, 2003

(87) PCT Pub. No.: WO02/34953

PCT Pub. Date: May 2, 2002

(65) Prior Publication Data

US 2004/0072147 A1    Apr. 15, 2004

Related U.S. Application Data

(60) Provisional application No. 60/242,903, filed on Oct. 24, 2000, now abandoned.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search ................ None
See application file for complete search history.

(56) References Cited

OTHER PUBLICATIONS

Jones, Virology, vol. 197, pp. 449-454, 1993.*
Ellinger et al. J.of Gen. Virol. vol. 74, pp. 495-500, 1993.*
Alexander J. Ryncarz et al.; Development of a High-Throughput Quantitative Assay for Detecting Herpes Simplex Virus DNA in Clinical Samples; Journal of Clinical Microbiology, Jun. 1999, p. 1941-1947.
Pamela M. Holland et al.; "Detection of specific polymerase chain reaction product by utilizing the 5'→3' exonuclease activity of Thermus aquaticus DNA polymerase", Proc. Natl. Acad. Sci. USA vol. 88, pp. 7276-7280, Aug. 1991 Biochemistry.
Database EMBL "Online!" EBI, Hinxton, Cambridgeshire, U.K.; Jun. 30, 1993, H.Q. Pan et al. "Cloning vector cosmid svPHEP DNA sequence encoding beta-lactamase and HSV thymidine kinase genes" XP002247595.
Francis Lallemand et al. "Quantitative Analysis of Human Herpesvirus 8 Viral Load Using a Real-Time PCR Assay", Journal of Clinical Microbiology, vol. 38, No. 4, Apr. 2000, p. 1404-1408.
Harald H. Kessler et al. "Detection of Herpes Simplex Virus DNA by Real-Time PCR" Journal of Clinical Microbiology, vol. 38, No. 7, Jul. 2000, p. 2638-2642.

* cited by examiner

*Primary Examiner*—Jeanine A. Goldberg
(74) *Attorney, Agent, or Firm*—Foley & Lardner LLP

(57) ABSTRACT

In clinical settings as well as in a drug development context, human herpes viruses can be detected, and even quantified, by the use of a real time PCR-based assay. An informatics analysis of existing gene sequences from different HHV types or strains is used to identify a target segment within a gene. A probe oligonucleotide and at least two primer oligonucleotides are then designed for selectively directing the amplification, in the course of a single amplification reaction, of the target segment of a particular HHV type or strain. This method is capable of an unprecedented level of discrimination among the following HHV types and strains: HHV1, drug resistant HHV1, HHV2, drug resistant HHV2, HHV3, HHV4*a*, HHV4*b*, HHV5, HHV6*a*, HHV6*b*, HHV7, and HHV8.

17 Claims, 4 Drawing Sheets

DETECTION AND QUANTIFICATION OF HUMAN HERPES VIRUSES

BACKGROUND OF THE INVENTION

The present invention relates generally to the detection of human herpes viruses and, more particularly, to measuring human herpes viral infection in real time, for example, for purposes of clinical testing, drug screening and infection prognostication, inter alia.

Eight human herpes viruses are recognized presently, and these are divided into three sub-families, as shown below.

|  |  |
|---|---|
| 1. Alpha herpes virinae | |
| Simplex virus | human herpes virus 1 (HHV1); human herpes virus 2 (HHV2) |
| Varicellovirus | human herpes virus 3 (HHV3) |
| 2. Beta herpes virinae | |
| Cytomegalovirus | human herpes virus 5 (HHV5) |
| Roseolovirus | human herpes virus 6 (HHV6); human herpes virus 7 (HHV7) |
| 3. Gamma herpes virinae | |
| Lymphocryptovirus | human herpes virus 4 (HHV4) |
| Rhadinovirus | human herpes virus 8 (HHV8) |

Various of these viruses are associated with human pathologies. For instance, HHV4 or "Epstein-Barr virus" (EBV) is associated with infectious mononucleosis, also known as "glandular fever." HHV4 is linked as well with oncogenesis with regard, for example, in Burkitt's lymphoma and nasopharyngeocarcinoma. Additionally, HHV4 is found in immune-suppressed patients and in patients suffering from Hodgkin's disease.

HHV5 is known as "cytomegalovirus" and causes infections in the lungs of immune-suppressed persons. HHV5 infection is less common than HHV4, and yet approximately 80% of the population in the United Kingdom, for instance, experience HHV5 infection by mid-life. HHV5 is probably transmitted by means of saliva, sexual contact, droplets and blood transfusions. In addition, both HHV4 and HHV5 are believed to be associated with chronic-fatigue syndrome, a malady that may afflict as many as in six out of every 100,000 people.

HHV6 is associated with "roseola" and "infantum" infections in children and with immune-compromised patients. For example, AIDS patients exhibit HHV6 infection, although the significance of the HHV6 infection is unclear. HHV6 is susceptible to antiviral drugs. It is unclear, however, how antiviral drugs work against HHV6 or how resistance to such drugs develops. A significant aspect of HHV6 infection is its putative tie-in with multiple sclerosis (MS) and chronic fatigue syndrome (CFS), respectively.

Less is known about HHV7 and HHV8. No clear evidence for the direct involvement of HHV7 in any human disease has been reported. Studies indicate, however, that HHV7 may be associated with HHV6-related infections. In a related vein, HHV8 infection is believed to be associated with Karposi's Sarcoma.

Conventional techniques have several limitations that have retarded their use in elucidating the significance of human herpes virus infection in the development of several diseases, such as CFS. Prevailing methods are not sensitive for detection of specific types and strains of human herpes virus and for quantitation of specific human herpes viruses.

If an assay reveals a positive viral load, therefore, additional assays are required to detect specific human herpes viruses. As a consequence, several days may elapse before a patient is diagnosed. In addition, conventional techniques do not detect virus when viral levels are low, for example, at early stages of infection. Accordingly, clinical settings are hampered by a lack of sensitive methods to detect virus and lose valuable time before a patient can receive treatment.

Current methods also require large amounts of physiological samples, whereas only small amounts of samples from each patient are usually available for analysis. It is therefore difficult to generate reproducible measurements of viral levels from peripheral blood of patients. Additionally, small amounts of physiological samples may be difficult to obtain and can entail procedures risky to patients, as in the instance of cerebrospinal fluid, and therefore may not have not been available for routine testing in a clinical environment.

Conventional approaches in this area often involve the polymerase chain reaction (PCR), by which smaller amount of samples can be analyzed. PCR-based testing for human herpes virus has been limited, however, by long turnaround times. Moreover, the application of PCR to small samples can lead to an increase in error rates, because more amplification cycles are required for lesser amounts of sample. In addition, PCR-based results for human herpes viruses have appeared to lack reproducibility, given the conflicting date that are reported in the literature.

The absence of a treatment for many human herpes viruses is another important concern. There is no practical approach to monitoring the effectiveness of therapeutic agents in the clinical setting, reflecting the difficulties in testing for specific virus infections and, particularly, in quantitating viral levels. Furthermore, the lack of a suitable screening approach for such therapeutic agents detracts from the incentive to develop them.

These difficulties pertaining to conventional PCR-based approaches to diagnosis are illustrated by attempts to measure HHV6 infection. Reports on the use of PCR to measure HHV6 DNA in CFS and MS patients indicate that the viral levels thus detected depend upon the particular methodology employed. For example, Locatelli et al., WO 00/29613, used real-time quantitative PCR to obtain HHV 6-positive results in 34% of cerebral spinal fluid (CSF) and 18% of plasma samples from MS patients. Similarly, Soldan et al., *Nature Med.* 3: 1394-1397 (1997), used a nested PCR procedure and found that a significant number of plasma samples from MS patients were HHV6-positive. On the other hand, other labs also employing PCR-based assays reported much lower levels of HHV 6 DNA in MS patients. For example, Ablashi et al., *J. Clinic. Virol.* 16(3): 179-191 (2000), reported that 9.1% of CSF and 4.5% of plasma samples tested positive for HHV 6, whereas Taus et al., *Acta. Neurol. Scand.* 101(4): 224-228 (2000), reported that HHV6 DNA was reported absent from CSF drawn from MS patients.

Similarly, other groups relying on PCR-based methods have reported low amounts of HHV6 in CFS patients. Secchiero et al., *J. Infect. Dis.* 171: 273-280 (2000), for example, reported that 2.6% of plasma samples from CFS patients were HHV6-positive.

In summary, prevailing PCR methods for human herpes virus yield irreproducible results, which complicate efforts to diagnose and treat HHV infection. Further, these methods have not addressed the need for a fast throughput assay, which is essential in clinical settings. As noted, moreover, there is a lack of therapeutic measures against many human herpes viruses, such as HHV6a and HHV6b, in part due to the absence of a ready technique for detecting them.

SUMMARY OF THE INVENTION

Accordingly, an urgent need exists for a rapid, sensitive method for the accurate reproducible detection and quantification of human herpes viruses in patient samples and pooled human plasma. Concomitantly, the ability to detect and quantify those viruses would allow assessment of the effect of new antiviral agents.

The present invention addresses these needs by utilizing an innovative bioinformatics approach which allows design of sequence-specific primers and probes to measure the presence of a specific viral gene and to distinguish between viral subtypes, such as HH4a and HHV4b or HHV6a and HHV6b. The primers and probes selected through this approach further allow discrimination among various HHV strains. Avoiding the deficiencies of conventional technologies, the present invention provides a methodology to detect and to quantify human herpes viruses in real time (typically, less than one hour), thereby allowing assessment, for example, of treatment options for individual patients in a clinical setting. By combining target-gene amplification and target-gene detection in a single reaction, the invention improves the rate and sensitivity for evaluating the presence or absence of specific strains of human herpes viruses. The improved ability to diagnose HHV offered by the invention is exemplified by the detection of a particular HHV type in individuals that was undetectable by conventional methodologies.

Target amplification requires the use of forward and reverse primers that direct Taq Polymerase-catalyzed formation of the complementary strand of the target. Detection is effected through the use of an internal fluorogenic probe that hybridizes to the target between the two primers. In one embodiment of the invention, the 5'-3' exonuclease activity of Taq Polymerase cleaves a fluorescence quencher moiety from the bound probe as it catalyzes the synthesis of the complementary strand. The cleaved probe dissociates and is detected through an increase in its fluorescence emission.

The present invention thus provides a method for detecting infection by a particular type or strain of HHV in a sample from an individual suspected of having HHV, comprising:

(a) performing an informatics analysis of existing gene sequences from different HHV types or strains to identify a target segment within the gene;
(b) selecting a probe oligonucleotide and at least two primer oligonucleotides capable of selectively directing the amplification, in the course of a single amplification reaction, of the target segment of the particular HHV type or strain;
(c) amplifying the target segment in the course of a single amplification reaction; and
(d) interpolating the number of HHV viruses of the particular type or strain in the sample by comparing the number of amplification cycles required for detection of the target segment to the number of amplification cycles required to detect a known quantity of the target segment. In one embodiment, the expression of the gene from different HHV types or strains is indicative of active HHV infection.

The method for detecting HHV infection specifically may amplify a target segment selected from the group consisting of:

(1) a target segment of an HHV1 tk gene comprising SEQ ID NO: 48, using primers and a probe having sequences set forth in SEQ ID NOS: 1, 2, and 3;
(2) a target segment of an HHV2 tk gene comprising SEQ ID NO: 49, using primers and a probe having sequences set forth in SEQ ID NOS: 4, 5, and 6;
(3) a target segment of a drug resistant HHV2 tk gene comprising SEQ ID NO: 50, using primers and a probe having sequences set forth in SEQ ID NOS: 7, 8, and 9;
(4) a target segment of an HHV3 tk gene comprising SEQ ID NO: 52, using primers and a probe having sequences set forth in SEQ ID NOS: 13, 14, and 15;
(5) a target segment of an HHV5 intermediate early gene comprising SEQ ID NO: 56, using primers and a probe having sequences set forth in SEQ ID NOS: 25, 26, and 27;
(6) a target segment of an HHV7 glycoprotein B gene comprising SEQ ID NO: 60, using primers and a probe having sequences set forth in SEQ ID NOS: 42, 43, and 44;
(7) a target segment of an HHV8 K1 gene comprising SEQ ID NO: 61, using primers and a probe having sequences set forth in SEQ ID NOS: 45, 46, and 47;
(8) a target segment of an HHV4a EBNA gene comprising SEQ ID NO: 54, using primers and a probe having sequences set forth in SEQ ID NOS: 19, 20, and 21;
(9) a target segment of an HHV4b EBNA gene comprising SEQ ID NO: 55, using primers and a probe having sequences set forth in SEQ ID NOS: 22, 23, and 24;
(10) a target segment of an HHV6a intermediate early gene comprising SEQ ID NO: 59, using primers and a probe having sequences set forth in SEQ ID NOS: 36, 37, and 38;
(11) a target segment of an HHV6b intermediate early gene comprising SEQ ID NO: 58, using primers and a probe having sequences set forth in SEQ ID NOS: 39, 40, and 41;
(12) a target segment of a drug resistant HHV1 or a drug resistant HHV2 tk gene comprising SEQ ID NO: 51, using primers and a probe having sequences set forth in SEQ ID NOS: 10, 11, and 12;
(13) a target segment of an HHV4 LMP-1 gene comprising SEQ ID NO: 53, using primers and a probe having sequences set forth in SEQ ID NOS: 16, 17, and 18; and
(14) a target segment of an HHV6 glycoprotein B gene comprising SEQ ID NO: 57, using primers and a probe having sequences set forth in SEQ ID NOS: 33, 34, and 35.

Also provided is a method for cloning a segment of genomic HHV viral DNA, comprising:

(a) selecting a candidate HHV gene, wherein expression of the candidate gene is predictive of active HHV infection;
(b) performing an informatics analysis of existing gene sequences from different HHV types or strains to identify a target segment within the gene;
(c) selecting a probe oligonucleotide and at least two primer oligonucleotides capable of selectively directing the amplification, in the course of a single amplification reaction, of the target segment of the particular HHV type or strain;
(d) using said probe oligonucleotide and at least two primer oligonucleotides to amplify the target segment from isolated genomic DNA from the particular HHV type or strain; and
(e) inserting the amplified target segment into a vector.

A polynucleotide molecule of the invention may be selected from the group consisting of SEQ ID NO: 1 through SEQ ID NO: 60, and SEQ ID NO: 61. Also provided are vectors that comprise a fragment of a gene that encodes:

(1) an HHV1 thymidine kinase protein, wherein the fragment comprises (i) a polynucleotide molecule having the sequence set forth in SEQ ID NO: 48, and (ii) up to 30 nucleotide base pairs at the 3' or 5' end of the polynucleotide molecule;

(2) an HHV2 thymidine kinase protein, wherein the fragment comprises (i) a polynucleotide molecule having the sequence set forth in SEQ ID NO: 49, and (ii) up to 30 nucleotide base pairs at the 3' or 5' end of the polynucleotide molecule;

(3) a thymidine kinase protein from a drug-resistant HHV2, wherein the fragment comprises (i) a polynucleotide molecule having the sequence set forth in SEQ ID NO: 50, and (ii) up to 30 nucleotide base pairs at the 3' or 5' end of the polynucleotide molecule;

(4) a thymidine kinase protein from a drug-resistant HHV1 or a drug resistant HHV2, wherein the fragment comprises (i) a polynucleotide molecule having the sequence set forth in SEQ ID NO: 51, and (ii) up to 30 nucleotide base pairs at the 3' or 5' end of the polynucleotide molecule;

(5) an HHV3 thymidine kinase protein, wherein the fragment comprises (i) a polynucleotide molecule having the sequence set forth in SEQ ID NO: 52, and (ii) up to 30 nucleotide base pairs at the 3' or 5' end of the polynucleotide molecule;

(6) an HHV4a latent membrane protein-1 or an HHV4b latent membrane protein-1, wherein the fragment comprises (i) a polynucleotide molecule having the sequence set forth in SEQ ID NO: 53, and (ii) up to 30 nucleotide base pairs at the 3' or 5' end of the polynucleotide molecule;

(7) an HHV4a nuclear protein EBNA2, wherein the fragment comprises (i) a polynucleotide molecule having the sequence set forth in SEQ ID NO: 54, and (ii) up to 30 nucleotide base pairs at the 3' or 5' end of the polynucleotide molecule;

(8) an HHV4b nuclear protein EBNA2, wherein the fragment comprises (i) a polynucleotide molecule having the sequence set forth in SEQ ID NO: 55, and (ii) up to 30 nucleotide base pairs at the 3' or 5' end of the polynucleotide molecule;

(9) an HHV5 intermediate early protein, wherein the fragment comprises (i) a polynucleotide molecule having the sequence set forth in SEQ ID NO: 56, and (ii) up to 30 nucleotide base pairs at the 3' or 5' end of the polynucleotide molecule

(10) an HHV6a glycoprotein B or an HHV6b glycoprotein B, wherein the fragment comprises (i) a polynucleotide molecule having the sequence set forth in SEQ ID NO: 57, and (ii) up to 30 nucleotide base pairs at the 3' or 5' end of the polynucleotide molecule;

(11) an HHV6a intermediate early protein, wherein the fragment comprises (i) a polynucleotide molecule having the sequence set forth in SEQ ID NO: 59, and (ii) up to 30 nucleotide base pairs at the 3' or 5' end of the polynucleotide molecule;

(12) an HHV6b intermediate early protein, wherein the fragment comprises (i) a polynucleotide molecule having the sequence set forth in SEQ ID NO: 58, and (ii) up to 30 nucleotide base pairs at the 3' or 5' end of the polynucleotide molecule;

(13) an HHV7 glycoprotein B, wherein the fragment comprises (i) a polynucleotide molecule having the sequence set forth in SEQ ID NO: 60, and (ii) up to 30 nucleotide base pairs at the 3' or 5' end of the polynucleotide molecule; or

(14) an HHV8 K1 glycoprotein, wherein the fragment comprises (i) a polynucleotide molecule having the sequence set forth in SEQ ID NO: 61, and (ii) up to 30 nucleotide base pairs at the 3' or 5' end of the polynucleotide molecule.

The invention further provides a fluorogenic probe that comprises:

(i) a sequence selected from the group consisting of SEQ ID NOS: 3, 6, 9, 12, 15, 18, 21, 24, 27, 30, 31, 32, 35, 38, 41, 44, and 47; (ii) a fluorescent reporter moiety covalently attached to the probe; and (iii) a fluorescence quencher moiety covalently attached to the probe.

BRIEF DESCRIPTION OF THE DRAWINGS

Table 1 lists representative primers, probes, and amplicons selected by the inventive bioinformatics approach. These primers, probes, and amplicons are used for the specific detection of any one of human herpes viruses HHV1, HHV2, acyclovir-resistant HHV2 (DR HHV2), HHV3, HHV4a, HHV4b, HHV5, HHV6a, HHV6b, HHV7 and HHV8.

Table 2 provides primers, probes, and amplicons useful for screening assays to detect multiple types of HHV. They can be used to detect combinations of (1) HHV1 and HHV2; (2) HHV4a and HHV4b; or (3) HHV6a and HHV6b.

FIG. 1 illustrates the impact of the bioinformatics approach of the invention on the choice of primers and probe.

Positive signals are elicited using HHV4 genomic DNA with primers and probe complementary to the LMP-1 gene of HHV4 and HHV6 genomic DNA with primers and probe complementary to the gB gene of HHV6. No positive signal is detected when HHV6 genomic DNA is used with primers and probe complementary to the LMP-1 gene of HHV4 or when HHV4 genomic DNA is used with primers and probe complementary to the gB gene of HHV6. The primers and probe alone also showed no positive signal.

Figure 2A:
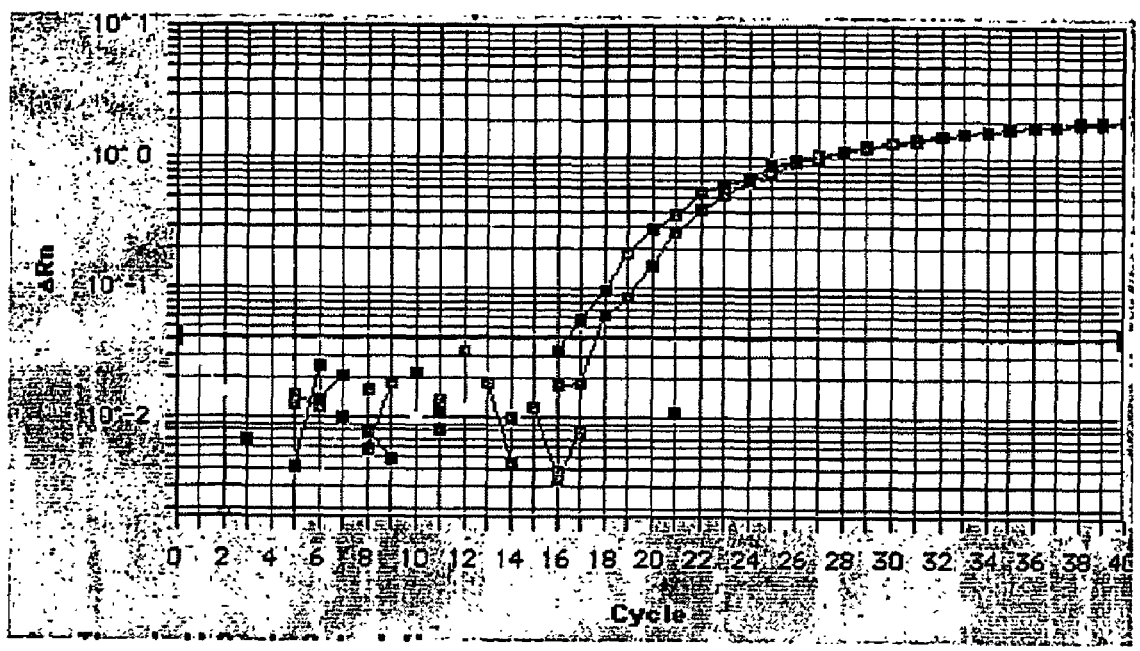
FIG. 2A depicts real time detection of an LMP-1 gene of HHV4, using an embodiment of the invention that is tailored to the TaqMan® platform. Fluorescence emission intensity ($\Delta R_n$) is plotted against PCR amplification cycle number. The number of PCR cycles required for the increase in emission intensity is proportional to the amount of target sequence in the reaction. $C_T$ demarcates the threshold cycle where the emission intensity associated with a "positive" detection of the target sequence exceeds a preset baseline value (horizontal line).
Figure 2B:
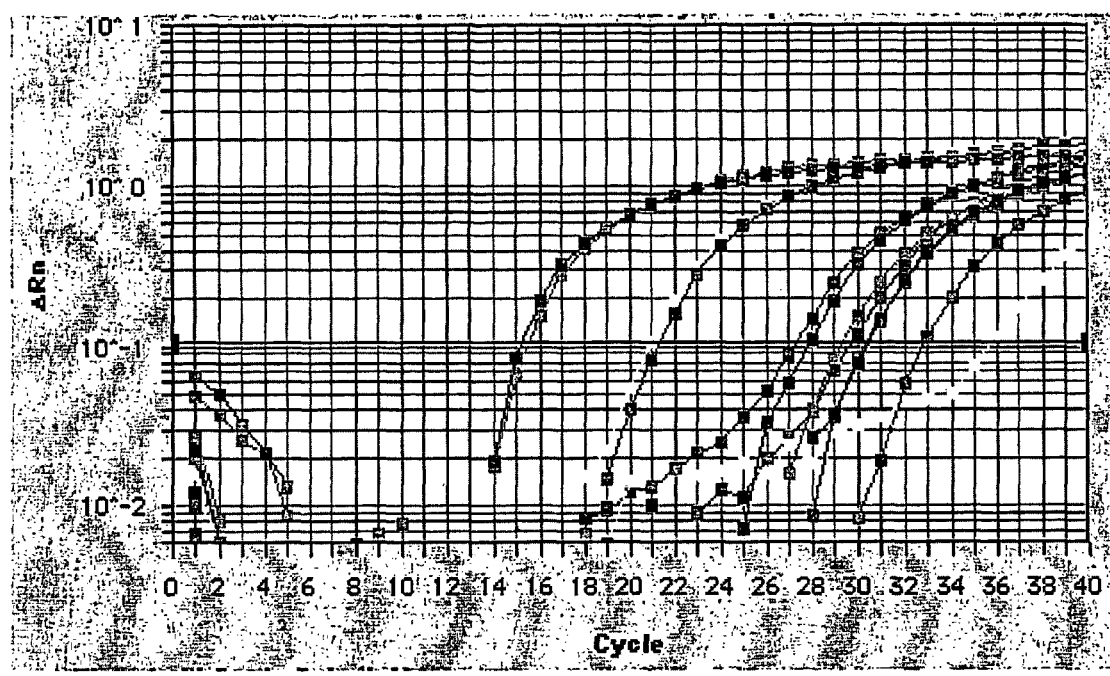
FIG. 2 demonstrates that primers and probes selected by the inventive bioinformatics approach react specifically with the selected target gene.

FIG. 2B depicts assays using the cloned LMP-1 gene amplicon of HHV4 at various known concentrations.

Assays of the type depicted in FIG. 2B can be used to create a calibration curve, such as shown in FIG. 2C. The amount of target sequence present in an unknown sample can then be interpolated by determining a $C_T$ value for the sample. For example, from the curve shown in FIG. 2C, a sample yielding a $C_T$ of 20 cycles is inferred to contain about $5 \times 10^4$ copies of HHV.

DETAILED DESCRIPTION OF THE PREFERRED EMBODIMENTS

The procedure of the invention allows accurate and sensitive diagnosis of HHV infection in patients. Unlike conventional procedures, infection by one strain of a specific type of HHV can be distinguished from infection by another strain of the same HHV type. For example, the detection procedure of the invention not only can distinguish infection by HHV6 from infection by HHV7, but it can distinguish infection by HHV6a from infection by HHV6b. Further, the inventive procedure can detect infection by HHV that cannot be detected by conventional PCR approaches.

An HHV gene is detected within a biological sample by selective amplification of a target sequence within the gene, using a set of two oligonucleotide primers and a fluorogenic hybridization probe. The advantageous sensitivity and selectivity of the method of the invention arise from the procedure by which both the target sequence and the primers and probe sequences are chosen.

The target sequence can be from any HHV gene for the purpose of the invention; however, the expression of some HHV genes more closely parallels viral load in an infected individual. Such genes are preferred as the source of the target sequence, because the number of copies of such genes in a biological sample from the infected individual is more indicative of the level of HHV infection. Genes that fall within this category include but not limited to the *thymidine kinase* gene (tk gene), the *Intermediate Early* gene, and some structural genes, such as the *glycoprotein B* gene. See generally, Weir, *Gene* 271: 117-30.

Once an HHV gene is selected, a target segment within the gene is chosen for amplification. Selection of this target segment requires a comparison of available DNA sequences of the target gene from different HHV types and strains. A growing number of DNA sequences for HHV genes from various HHV types and strains are available on public databases, such as GenBank or EMBL. These sequences are aligned using any number of well known algorithms, such as the Smith-Waterman algorithm, which is described in Waterman, *Bulletin of Mathematical Biology* 46:473-500 (1984)).

Figure 1A:
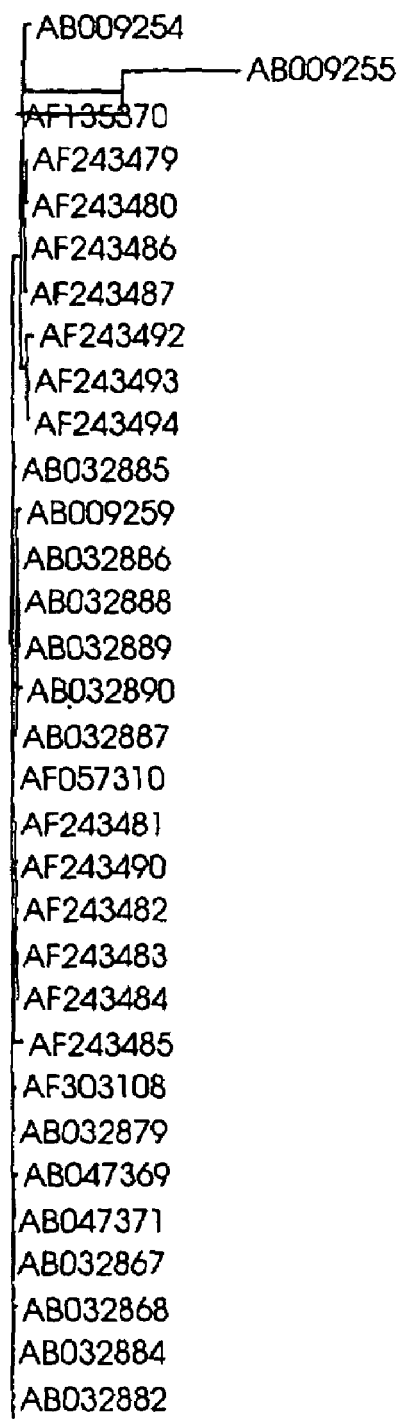
FIG. 1A is a phylogenetic tree representing genetic relationships among *thymidine kinase* (tk) gene sequences of different HHV1 strains, which are identified by Genbank accession number. Horizontal lines connecting pairs of sequences indicate relative sequence homology. (A shorter line indicates greater sequence homology.) Examination of the phylogenetic relationship between gene sequences and the extent of sequence homology informs the selection of primers and probes that can be used to detect the gene DNA of the various HHV1 strains.
Figure 1B:
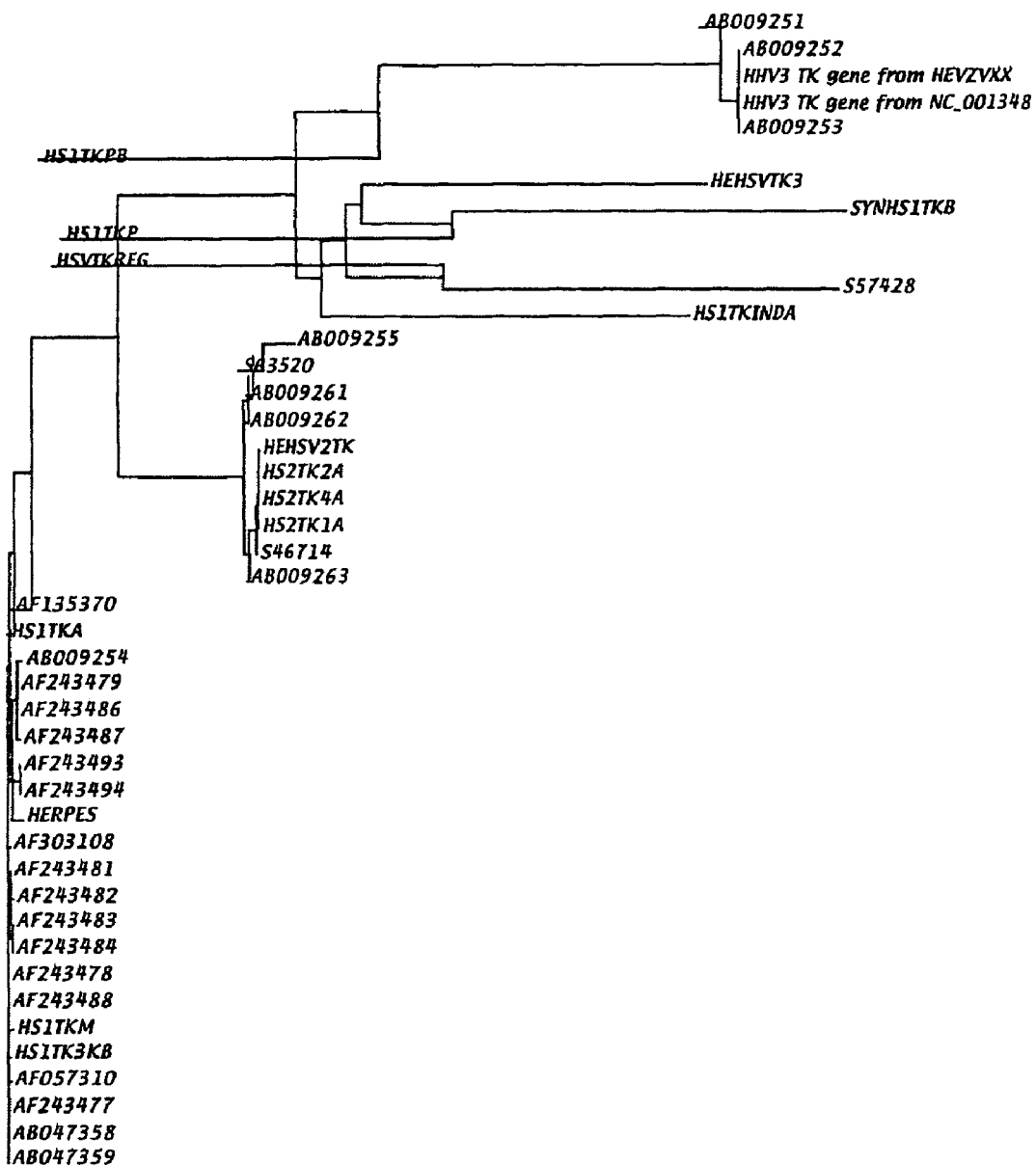
FIG. 1B shows relationships among tk gene sequences from HHV1, HHV2, and HHV3. From these relationships, primers and a probe sequence can be designed to detect all HHV1 tk sequences (left cluster). Alternatively, by altering the primer and probe sequences, an assay can be designed to detect both HHV1 and HHV2 sequences (middle cluster), given the relative sequence identity among these sequences. By contrast, HHV3 strains (right cluster) show poor sequence conservation at this target site, and they are less identical to either HHV1 or HHV2 sequences. Accordingly, the phylogenetic analysis predicts that this particular target would be a poor choice either to detect collectively HHV3 strains or to screen for the combined presence of HHV1, HHV2 and/or HHV3.

Comparison among HHV sequences is further refined by performing an informatics analysis of existing gene sequences from different HHV types or strains to identify a target segment within the gene. This informatics analysis is based on defining phylogenetic relationships between sequences. When multiple sequences are aligned, gaps are commonly inserted to optimize the alignment over the length of the total sequence. The gaps reflect insertion, deletion, or substitution of base pairs in a sequence that arise during evolution. A phylogenetic analysis treats these gaps as "character information," in the sense that sequences that are closely related evolutionarily more likely will possess the same sequence insertions, deletions, or substitutions, when compared to other sequences. Thus, phylogenetic analysis predicts "clusters" of sequences, such as those depicted in FIGS. 1 and 2, that possess common sequence characteristics. For example, in a given target segment, a sequence of GATC may be common to all HHV1 sequences, whereas the corresponding sequence may be CTAG in all HHV2 sequences. Phylogenetic analysis thus classifies sequences by these related characteristics, allowing identification of sequence segments that may be useful to distinguish various HHV types and strains.

Phylogenetic algorithms are reviewed in Phillips et al., *Mol. Phylogenet. Evol.* 16: 317-30 (2000) and Sanderson et al., *Systematic Zoology*, 39: 414-20 (1990). Vector NTI Alignment™ (InforMax, Inc., Rockville, Md.) is exemplary of the available software programs that can be used for phylogenetic analysis, pursuant to the present invention.

With respect to the present invention, the phylogenetic analysis identifies sequences useful for the specific detection of a HHV type or strain. The distinct clustering of HHV1 sequences and HHV2 sequences depicted in FIG. 2, for example, predicts that this particular target segment will be useful in distinguishing HHV1 infection from HHV2 infection. Knowing the sequences for this stretch of DNA, oligonucleotides can be designed that hybridize to HHV1 sequences, but not to HHV2 sequences. This design is keyed to the "character information" identified by phylogenetic analysis. Referring to the example used above, an oligonucleotide that is complementary to GATC will hybridize to all HHV1 sequences, but it likely will not hybridize to any HHV2 sequence, because of the four base pair mismatches over the corresponding four base pair region.

In accord with the invention, each of three oligonucleotides must hybridize to the target sequence to direct its amplification: a forward primer, a reverse primer, and a labeled internal probe that hybridizes to the target between the two primers. The specificity of detection is conferred through the hybridization of the internal probe to the target sequence. It is well known in the art to design a probe that will hybridize to a specified target region, under a given set of conditions. See, for example, Grove, *J. Biomolec. Techniques* 10(1) (1999). Since the conditions under which PCR reactions are conducted are all more or less the same, the base pair composition of the probe is varied so that it hybridizes specifically to the desired sequence. That is, the probe is designed to hybridize to the specified target region by varying the complementarity between the probe and the target sequence.

The DNA sequence of a useful target segment may not be available for each HHV strain. However, using the phylogenetic approach of the invention, the degree of sequence identity of such a strain can be estimated from its phylogenetic relationship with closely related HHV strains. Thus, the method of the invention can be applied to HHV strains for which complete sequence data is unavailable.

HHV infection can be diagnosed by assaying any bodily fluid, such as saliva, serum, plasma, blood, urine, or cerebrospinal fluid. The inventive procedure also can be used to detect HHV in other sources, e.g. cell culture extracts, tissue samples, plasma fractionation products, and pharmaceuticals destined for human or animal use.

Further, the inventive approach can be used to create a screening platform to analyze the effectiveness of pharmaceuticals by measuring the ability of anti-viral agents to mediate human herpes virus propagation. In situ anti-viral activity analysis is amenable to a rapid throughput format, which enhances efficiency in identification of test agents that inhibit viral propagation. In addition to determining specific activity of anti-viral agents, purification of promising anti-viral agents can also be tracked. The present invention thus circumvents problems endemic to ex vivo testing, such as drug toxicity and side effects.

A preferred embodiment of the invention adapts a PCR-based, thermal cycling amplification technology, such as the TaqMan® (Applied Biosystems) assay, to detect, distinguish, and quantitate human herpes viral DNA. A TaqMan® assay combines PCR and probe-hybridization reactions into one reaction and is amenable to real-time analysis by means of a detection device, such as the ABI 7700, a product of Applied Biosystems (Foster City, Calif.). See Holland et al., *Proc. Nat'l Acad. Sci. U.S.A.* 88: 7276-80 (1991), and Livak et al., PCR METHODS AND APPLICATIONS 4: 357-362, Cold Spring Harbor Laboratory Press (1995).

Such an assay requires at least three oligonucleotides for the analysis of each target nucleic acid sequence. The sequences of forward and reverse primers are complementary to the ends of the target nucleic acid sequence. A probe sequence is complementary to the sequence found between the ends of the target nucleic acid sequence. A "forward primer" and a "reverse primer" provide a template for polymerase-catalyzed amplification of the target nucleic acid sequence, when hybridized to the target. A single-stranded oligonucleotide is required for target detection and is referred to as the "probe" or "detection probe" or "internal oligonucleotide" or "internal oligonucleotide probe."

The TaqMan® technique combines two reactions into a single reaction format: (1) nucleic acid probe hybridization to detect a specific target nucleic acid sequence and (2) PCR to amplify a target nucleic acid sequence. First, a probe is synthesized so as to contain two distinct moieties, a fluorogenic reporter group a suitable fluorescence quenching group. Through fluorescence resonance energy transfer, the quencher reduces the fluorescence emission of the fluorescent reporter group. In the TaqMan® process, two primers and a probe hybridize to the target template DNA, which then allows polymerase-catalyzed synthesis of the complementary strand of the target. In one embodiment, the 5'-3' exonuclease activity of Taq Polymerase cleaves the quencher moiety from the bound probe as it catalyzes complementary strand synthesis, causing the fluorescence emission of the probe to increase, since the reporter is no longer quenched. An increase in the fluorescent signal during the amplification reaction thus depends on the hybridization of both the fluorogenic probe and primers to the target sequence. Target discrimination is enhanced because spurious amplification caused by non-specific primer hybridization is not detected. See Lee et al., *Nucleic Acids Res.* 21: 3761-3766 (1993); TaqMan® PCR reagent Kit, Document No. 430449, published by Applied Biosystems.

The probe is labeled by covalently linking fluorescent tags to either end of the probe. A "fluorescent reporter," such as, FAM (6-carboxy-fluorescein) or TET (6-carboxy 4, 7, 2', 7'-tetrachloro-fluoroscein) is covalently linked to the 5'-end of the detection probe. A "quencher dye," such as TAMRA (6-carboxy-N,N,N',N'-tetramethyl-rhodamine), is attached to the detection prove. See, for example, Holland et al., *Proc. Natl. Acad. Sci. USA* 88: 7276-80 (1991); and Perkin-Elmer, AmpliTaq Gold™ Product Insert, Rev. 3 (1996). An "internal oligonucleotide" or "detection probe" or "probe" linked to a "fluorescent reporter" and "quencher" is called a "fluorogenic probe" or an "internal fluorogenic probe."

In accordance with the invention, fluorescent reporters and quenchers other than those mentioned above can be employed in an assay of the present invention, see U.S. Pat. No. 5,538,848 to Livak et al. Also feasible are other means for generating fluorescent signals, as by the use of ethidium bromide or another intercalator. See Holland et al. (1991), supra.

Probe sequences and labeling moieties can be adapted to platforms other than TaqMan®. A common platform is light cycling, which uses other types of fluorescent probes well known in the art, including "molecular beacons," "smart probes," "scorpions," or "eclipse probes." See, for example, Thelwell et al., *Nuc. Acids Res.* 28: 3752-61 (2000). "Smart probes," for example, are described in Knemeyer et al., *Anal. Chem.* 72: 3717-24 (2000). These probes report the presence of complementary target sequences by a strong increase in fluorescence intensity upon hybridization to the complementary sequence on the target. The smart probes consist of a fluorescent dye, such as oxazine dye JA242, that is quenched by means of complementary guanosine residues at the terminus of a hairpin oligonucleotide. Specific hybridization to a target sequence induces a conformational change in the smart probe forcing the fluorescent dye and the guanosine residues apart, thereby increasing the fluorescence intensity.

Detection devices are available for measuring changes in fluorescence emission intensity during an amplification according to the present invention. Illustrative of such devices are: the ABI 7700 of Applied Biosystems; the BDProbeTecET fluorescent reader of Becton Dickinson Microbiology Systems (Sparks, Md.), see Little et al., *Clin. Chem.* 45: 777-784 (1999); and the "SmartCycler" of Cepheid (Sunnyvale, Calif.). This measurement is done in real-time, i.e., in the same time frame that the amplificatio reaction. Other methods are available for gauging changes in fluorescence which result from probe digestion. Exemplary of such alternative techniques is fluorescence polarization, as described, for example, in U.S. Pat. No. 5,593,867 to Walker et al. Fluorescence polarization distinguishes larger from smaller molecules based on different rates of molecular tumbling.

By way of illustration, the ABI 7700 "Sequence Detection" software employs three terms to express results: $R_n$ (normalized reporter signal), $\Delta R_n$ (normalized reporter signal minus baseline signal), and $C_T$ (threshold cycle). $R_n$ represents fluorescence signal from reporter dye divided by fluorescence signal of a passive reference dye. $R_n$ and $\Delta R_n$ increase as the amount of amplified product accumulates in the reaction. If initial number of copies of a target nucleic acid sequence in a reaction are high, then fewer number of cycles of amplification are required to reach a detectable level of fluorescence.

On a graph of $R_n$ vs. cycle number, the threshold cycle ($C_T$) occurs where the application begins to detect an increase in fluorescence emission signal associated with exponential growth of PCR product. Therefore, $C_T$ represents a detection threshold for a sequence detector. In the ABI 7700 instrument, for example, $C_T$ depends on number of nucleic acid target sequences at the start of PCR, efficiency of DNA amplification during PCR, and efficiency of the cleavage of the fluorogenic probe. Although the ABI 7700 device determines $C_T$ values from fluorescence measurements, other signals, as noted previously, can be used to measure $C_T$ values.

For the inventive assay, a calibration curve is prepared using "standards," which are samples containing a known number of copies of a target nucleic acid sequence. Independent reactions are performed, each containing a different standards. A graph or a "standard curve" of $C_T$ vs. LogN (starting copy number) is prepared using $C_T$ values from each of the reactions that involved a different amount of standard.

The number of copies of target nucleic acid sequence in a test sample is determined by interpolating $C_T$ values from a reaction containing the test sample onto the standard curve. In a preferred embodiment, a software program, such as the "Sequence Detection" application of the ABI 7700, generates a "standard curve" of $C_T$ vs. LogN (starting copy number) for all "standards" and then determines the starting copy number of unknowns by interpolation. Other software programs can be used in the present invention, such as the program within a BDProbeTecET instrument, which reports results through an algorithm as described by Little et al. (1999), supra. The determination of the number of copies of a target gene sequence in a test sample indicates the number of viruses or viral remnants in the test sample.

In accordance with the present invention, multiplex formats can be employed to detect more than one target nucleic acid sequence in a single reaction. For example, primers for more than one target gene, with the corresponding target-specific probes linked to different fluorescent reporters, can detect multiple targets in a single reaction.

EXAMPLE 1

Designing Primers and Probe for HHV1

This section details an application of the inventive bioinformatics approach to HHV1. GenBank lists more than 250 entries of interest for HHV1, including one entry for a complete genome, several open reading frames (ORFs). and plasmid clones. The tk gene of HHV1 was chosen as a target for assay development, because more than 100 tk gene entries were found in GenBank. In addition, tk gene activity is known to be a good marker of viral infection.

In the region of nucleotides 301-600 of the GenBank sequence entries for HHV1 tk gene, alignment of the sequences revealed few sequence differences, indicating that tk genes in different strains of HHV1 share close genetic relationships. Phylogenetic analysis (FIG. 1A) confirmed the likelihood of close genetic relationships within tk genes of different HHV1 strains.

A segment of the tk gene, referred to as "HHV1 tk gene amplicon" or "HHV1 tk amplicon" (SEQ ID NO 48; see Table 3A), was chosen for amplification, based on TaqMan® assay requirements for nucleotide content of primers and probes and for size of amplicon. By the same token, TaqMan® assay requirements for nucleotide content and oligonucleotide size guided the design of forward and reverse PCR primers for amplification of HHV1 tk amplicon, and probe sequence for specific detection of HHV1 tk amplicon.

Primer and probe sequences and their locations within the HHV1 tk gene are shown in Table 3A.

TABLE 3A

| HHV1 Thymidine Kinase (TK) Gene Primers and Probes | | | | |
|---|---|---|---|---|
| | Start | Length | Tm | Sequence |
| HHV1 Forward Primer | 358 | 20 | 60.10 | GTAATGACAAGCGCCCAGAT |
| HHV1 Reverse Primer | 545 | 20 | 59.94 | ATGCTGCCCATAAGGTATCG |
| HHV1 Probe | 412 | 20 | 59.65 | CGTTCTGGCTCCTCATATCG |

Amplicon Product Size: 188 (SEQ ID NO: 48)
SEQ ID NO: 1 GTAATGACAAGCGCCCAGAT Forward Primer HHV1
SEQ ID NO: 2 ATGCTGCCCATAAGGTATCG Reverse Primer HHV1
SEQ ID NO: 3 CGTTCTGGCTCCTCATATCG Probe HHV1

A GenBank BLAST search, effected with these primer and probe sequences (SEQ ID NO: 1-3), confirmed that they were unique and complementary to the HHV1 tk amplicon, SEQ ID NO 48.

The above-described bioinformatics approach, applied to identify the tk gene as a target for HHV1 virus, to identify the tk gene amplicon, and to design appropriate primers and probe for the HHV1 tk gene, likewise was used in the design of primers and probe for other human herpes viruses. Table 1 presents the results for each of HHV2, acyclovir-resistant HHV2 (DR HHV2), HHV3, HHV4a, HHV4b, HHV5, HHV6a, HHV6b, HHV7 and HHV8.

For some target genes, more than one primer or probe were designed to overcome sequence differences found to exist within different GenBank entries for the amplicon sequence, thereby to allow for detection of more strains of a virus.

EXAMPLE 2

Designing Primers and Probes for HHV1 and HHV2 Screening Assays

As detailed above, the present invention contemplates a bioinformatics approach to the design of primers and probe for screening assays that, pursuant to the invention, will detect multiple types of virus in the course of a single reaction. Use of a screen-assay format reduces the initial number of separate assays that should be required to test different types of virus. Once a screen assay tests positive, then separate assays are required to detect individual type of virus that were included in the screen-assay design.

This portion of this specification relates the development of a screening assay, according to the present invention, for detecting human herpes viruses HHV1, HHV2, and DR HHV2. To this end, the inventors chose the tk gene as the target; hence, the informatics approach described above was performed for the tk gene from the three mentioned viruses, respectively.

GenBank contained more than 100 entries for HHV1 and HHV2 tk genes, including two complete genomes. Incomplete tk gene entries as well as the portions of the complete genomes from HHV1 and HHV2 were aligned, again as described above. The resultant phylogenetic analysis (FIG. 1B) showed that tk gene sequences from HHV1 and HHV2 are closely related but are diverse from HHV3. Accordingly, HHV3 was excluded from the screen assay design.

Alignment of HHV1 and HHV2 tk genes showed several base pair differences, as well as regions containing fully homologous sequences. Therefore, degenerate primers and probe were prepared to overcome differences found in the tk gene sequences entries and, thereby, to allow for detection of multiple viral strains. See Table 3B for screen-assay primer and probe sequences, SEQ ID NOs 10, 11 and 12.

Nucleic acid sequences of screen assay primers and probe were queried, in a BLAST search, against GenBank to confirm that the sequences were unique and complementary to the intended target, the tk gene.

TABLE 3B

HHV1 and HIV2 Screen Assay
Primers and Probe Sequences

| | Tm | Length | Sequence |
|---|---|---|---|
| HHV1-2 Forward Primer | 62.0 | 20 | AGTTGCTGGCCCCCAACGG C |
| HHV1-2 Reverse Primer | 59.4 | 20 | AAACGTGCGCGCCAGGTCGC G |
| HHV1-2 Probe | 57.9 58.1 | 20 | TTTATCCTGGATTACGACCA G T |

Amplicon Product Size: 148 bp (SEQ ID NO: 51)
SEQ ID NO. 10 AGYTGCTGGCCCCCAACGG Forward Primer HHV1 + 2 screen
SEQ ID NO. 11 AAACGTGCGCGCCRGGTCGC Reverse Primer HHV1 + 2 screen
SEQ ID NO. 12 TTTRTCCTGGATTACGAYCA Probe HHV1 + 2 screen
Nucleotide degeneracy codes: T/C = Y, A/G = R Essentially the same approach to the design of screen-assay primers and probes was employed (i) for HHV4a and HHV4b and (ii) for HHV6a and HHV6b. Table 2 shows the primers and probes designed for these HHV4 and HHV6 screen assays.

EXAMPLE 3

Preparing Calibration Curves and Quantifying Number of Copies of Virus in a Sample It often will be the case that a polynucleotide can be purchased or synthsized that corresponds to the segment of the target gene which is selected, via the bioinformatics approach of the present invention. Alternatively, an amplicon selected by the bioinformatics procedure in the invention can be amplified from an extract of genomic DNA using the amplification primers described above and standard molecular biology techniques. The amplicon is cloned into a DNA construct, such as, plasmid pCR 2.1, a product of Invitrogen (Carlsbad, Calif.) that has a replication origin, to generate multiple copies of the cloned plasmid.

The cloned plasmid serves as a reference standard for calibration. ("Standards" are samples containing a known number of copies of a target nucleic acid sequence.) For calibration, inventive assays for concurrent amplification and detection of target gene sequence in the cloned plasmid is performed. Several reactions are performed such that individual reactions contain a different concentration of the cloned plasmid. The concentration of plasmid used in each reaction is used to calculate the number of copies of the target nucleic acid sequence in the reaction. A graph or a 'standard curve' of $C_T$ vs. LogN (starting copy number) is prepared using $C_T$ values from each of the reactions containing a different amount of cloned plasmid. For a test sample containing an unknown number of copies of the target gene sequence, the number of copies of the target sequence is determined by interpolating $C_T$ values from a reaction containing the test sample onto the standard curve. Determination of the number of copies of a target gene sequence in a test sample, in this manner, indicates the number of viruses or viral remnants in the test sample.

EXAMPLE 4

Assay for HHV4

In further illustration of the present invention, an assay is described for HHV4. HHV4 belongs to the gamma herpes virinae family and is commonly known as "Epstein Barr virus" (EBV) or "Lymphocryptovirus." HHV4 infection usually leads to polyclonal B-cell activation and benign proliferation that maybe sub-clinical or result in infectious mononucleosis, also referred to as "glandular fever." HHV4 infection is associated with oncogenesis, such as Burkitts lymphoma and nasopharyngeal carcinoma. HHV4 infection also is associated with B cell lymphomas in immunosuppressed patients, certain T cell lymphomas, and Hodgkin's disease.

HHV4 exhibits dual cell tropism: human B-lymphocytes, generally results in non-productive infection, epithelial cells, results in productive infection. Suitable animal host for experimental purposes are unavailable, instead transformed human cell-lines, HHV4-immortalized lymphoblastoid cell lines (LCL), are used for HHV4 replication/latency research. HHV4 gene expression in LCL is restricted to about nine of the approximately 100 genes encoded by HHV4. Genes expressed in LCL are referred to as "latent genes" because LCL are generally non-permissive for HHV4 replication. Six of the latent genes encode the nuclear antigens EBNA-1, EBNA-2, EBNA-3A, EBNA-3B, EBNA-3C and LP, whereas three others encode latent membrane proteins, LMP-1, LMP-2A and LMP-2B.

The process of cellular transformation by EBV is not fully understood. The most abundantly expressed HHV4 latent transcripts in LCL are non-polyadenylated RNA that do not encode proteins, but are involved in avoidance of interferons. EBNA-1, EBNA-2, EBNA-3A, EBNA-3C and LMP-1 are essential for HHV4-induced B-cell transformation; EBNA-LP and LMP-2A enhance transformation efficiency. All transforming proteins are not expressed in Burkitt's lymphoma and nasopharyngeal carcinoma, except EBNA-1, which is regularly detected. In addition, several tumors express LMP-1 and LMP-2.

The above-described bioinformatics approach was applied to HHV4, in order to allow for the detection of both strain types 1 and 2. Sequences from GenBank were aligned and compared with nearest-neighbor sequences. Based on the above information regarding gene expression in tumors, EBNA-1 and LMP-1 genes were chosen as targets to detect both HHV4 strains, and EBNA-1 sequence entries and 45 LMP-1 sequence entries were aligned.

The sequence of primers, probe and amplicon to amplify and detect LMP-1 gene of HHV4 in an assay of the invention are shown in Table 2, SEQ ID NOs 16, 17, 18 and 53. Nucleic acid sequences of assay primers and probe were queried, in a BLAST search, against GenBank to confirm that the sequences were unique and complementary to the intended target, the LMP-1 gene.

To confirm that primers and probe selected for the LMP-1 gene of HHV4 specifically detected only HHV4 viruses, we also performed assays using HHV6 genomic DNA and HHV4 primers and probes. Similarly, specificity of HHV6 primers and probe for HHV6 virus was confirmed using HHV4 genomic DNA in assays with HHV6 gB gene primers and probes. See Table 2, SEQ ID NOS 33, 34, 35, and 57, for primers, probe and amplicon to amplify and detect gB gene of HHV6. An assay is described below that entails amplification and detection of the HHV4 LMP-1 gene amplicon in the course of a single amplification reaction.

(A.) DNA Extraction

Clones of LMP 1 gene of HHV4 are not commercially available. Therefore, the inventors obtained HHV4 DNA, from strain B95-8, from the Centers for Disease Control (Atlanta, Ga.). Clones of HHV6 DNA are not commercially available and so viral genomic DNA was extracted from mammalian cell lysates infected with virus. Virus-infected mammalian cells were obtained from The Center for Disease Control.

The method for extracting DNA from $5 \times 10^7$ mammalian cells, using QIAamp spin columns (Qiagen catalog No. 51104), is as follows:
a. Add 125 µl ProK (20 mg/ml) to 1 ml of sample;
b. Add 1 ml of Qiagen Buffer AL and vortex;
c. Incubate at 70° C. for 10 minutes;
d. Add 1050 µl 100% EtOH and vortex;
e. Apply 635 µl of sample from step (d) to QIA amp spin column;
f. Centrifuge the spin column from step (e) at 8000 rpm for 1 minute;
g. Discard filtrate obtained after centrifugation in step (f);
h. Repeat steps (e), (f) and (g) as necessary to process the entire cell lysate;
i. Place spin column from step (h) in a clean 2 ml collection tube;
j. Add 500 µl of Qiagen Buffer AW1 to the column;
k. Centrifuge the column at 8000 rpm for 1 minute;
l. Place the column in a clean 2 ml collection tube;
m. Add 500 µl of Buffer AW2 to the column and centrifuge at maximum speed (5000×g) for 3 minutes;
n. Place the column in a clean 1.5 ml collection tube;
o. Elute DNA from the column twice using 200 µl of Qiagen Buffer AE (preheated to 70° C.) each time;
p. Incubate eluate at 70° C. for 5 minutes;
q. Centrifuge eluate at 8000 rpm for 1 minute and discard pellet;
r. To improve yield of DNA, perform a third elution and repeat step (o) by reusing the 400 µl solution from step (q); reheat the solution containing eluted DNA from the third elution at 70° C., centrifuge the third eluate at 8000 rpm for 1 minute and discard pellet.

(B.) Assay for Concurrent Amplification and Detection of Target:

In a preferred embodiment, the TaqMan® assay is used for concurrent amplification and detection of a target gene. The assay uses two amplification primers and one labeled probe oligonucleotide that are unique and complementary to the target sequence.

The solutions employed in the assay are: 2× TaqMan® Universal Master Mix (Perkin Elmer catalog No. PE 4304437), used at a final concentration of 1× in each assay; and, 100 mM dNTP Mix (25 mM each NTP; Perkin Elmer catalogue No. N808-0261), used at a final concentration of 1× in each assay. For both HHV4 and HHV6, the final concentration of each amplification primer in the assay was 300 nM and the final concentration of the fluorogenic probe was 200 nM. The assay was performed in reaction volume of 50 µl. Sample containing viral genomic DNA was added in a maximum final volume of 5 µl. If lesser than 5 µl of sample containing viral DNA was added to a reaction, then the volume was adjusted by addition of water. Amplification (polymerase chain reaction) was performed by adding 25 µl per reaction AmpliTaq Gold (Applied Biosystems catalog No. 4304437).

The assay was performed in an ABI 7700 instrument or ABI 7900HT instrument, programmed as follows: step (1) 50° C. for 2 minutes; 95° C. for 10 minutes; step (2) 40 cycles of amplification of the target nucleic acid sequence, with denaturation at 95° C. for 15 seconds and annealing/extending at 60° C. for 1 minute, in accordance with manufacturer's instructions (Applied Biosystems). If a target nucleic acid sequence is present, the fluorescence from the reaction changes during the course of the polymerase chain reaction. The ABI instruments detect the change in fluorescence in real-time during the amplification reaction.

In initial experiments, the inventors used HHV4 genomic DNA as template in the assay described above, with primers and probe corresponding to LMP-1 gene. The primers and probe for the LMP-1 gene, designed pursuant to the above-described bioinformatics approach, are shown in Table 2 as SEQ ID NOs 16, 17, and 18. The red squares and line in FIG. 2A depict assays implemented using HHV4 genomic DNA and LMP-1 gene primers and probe ($C_T$ value was reached in cycle 16).

Primers and probe sequences designed, according to the inventive approach, for the gB gene of HHV6 are shown in Table 2 as SEQ ID NOs 33, 34, and 35. FIG. 2A also depicts results obtained using HHV6 genomic DNA and primers and probe for the HHV6 gB gene (violet squares and line; $C_T$ value is reached in cycle 17). The other symbols in FIG. 2A represent controls in which the assay was carried out, for example, with genomic DNA of HHV6 virus and LMP-1 gene primers and probe.

Thus, FIG. 2A demonstrates that primers and probe designed for the HHV6 gB gene, specifically detect HHV6 DNA. FIG. 2A also demonstrates that HHV6 gB primers and probe recognize different nucleic acid target sequences on HHV6 DNA and HHV4 DNA, respectively. No amplification occurred when viral genomic DNA in the reaction was substituted with water ($C_T$ value is reached in cycle 40).

(C.) Assay Calibration

The foregoing data validate the use of HHV4 genomic DNA as a standard for assays according to the present invention. To provide a stable and continuing source of DNA, for use as a reference standard, a 121 base-pair amplicon (SEQ ID NO: 53) for a HHV4 LMP 1 gene segment was cloned between the M13R and M13F primer sequences in plasmid pCR 2.1 plasmid, a product of Invitrogen Corporation (San Diego, Calif.). In this context, "standard" denotes a sample that contains known copies of a nucleic acid sequence for amplification in an assay. The number of copies of a target sequence in a test sample is determined from a standard calibration curve, and indicates the copy number of viruses or viral remnants in the test sample.

FIG. 2B presents a graph of the inventive assay, implemented using cloned LMP-1 plasmid DNA and LMP-1 gene primers and probe. Different concentrations of cloned DNA were used in the assay. The concentration of cloned DNA used in individual assays was used to calculate the number of copies of HHV4 LMP-1 gene targets in each assay. In FIG. 2B, the number of copies of HHV4 LMP-1 gene targets used in individual reactions was varies from $10^8$ to 10. At the highest copy number ($10^8$), $C_T$ value was approximately 15; at the lowest copy number (10), $C_T$ value was approximately 35.

FIG. 2C presents a graph of a calibration curve for the cloned HHV4 LMP-1 gene amplicon. In FIG. 4C, $C_T$ values and the corresponding number of copies of LMP-1 gene were obtained from the graph in FIG. 2B. In FIG. 2C, the equation that fits the data is: $Y=-2.62(X)+36.87$, where 36.87 is the $C_T$ value at infinitely low DNA concentration. The results of calibration indicate a linear response in the range of 10 copies of amplicon DNA to $10^8$ copies of amplicon DNA, i.e. from $10^{-15}$ g to $10^{-9}$ g of DNA.

EXAMPLE 5

Screen Assay for HHV4a and HHV4b

The assay for the LMP-1 gene, described in Example I, detects both HHV4 strains that circulate in the human population. Similarly, the inventive approach was used to design primers and probe to distinguish the HHV4a strain from HHV4b, also known as "type 1" and "type 2," respectively.

The genomes of HHV4a and HHV4b are nearly identical. However, the predicted amino acid sequence of the genes that code for the Epstein-Barr nuclear antigens, EBNA-2, EBNA-3A, EBNA-3B, and EBNA-3C differ between the two types of virus. The predicted primary amino acid sequence of virus type HHV4a differs from that of virus type HHV4b by 47%, 16%, 20%, and 28%, respectively. However, most sequence information for HHV4, as reflected in GenBank entries, are related to genes that are virtually identical among the two strains, such as the latent membrane proteins (LMP-1 and LMP-2A), and EBNA-1. Moreover, few of the sequence entries include information regarding the HHV4 strain used to derive the sequence.

As described above, a region from the LMP-1 gene was developed as the target to detect and quantify both HHV4 strains. The inventors likewise chose EBNA2 gene for screen assay development to distinguish between HHV4a and HHV4b strains. Of the eight GenBank entries for EBNA2 gene of HHV4, two contained very short portions (less than 200 bp) corresponding to the EBNA2 gene coding region (see locus HS4NA21 and HS4NA22 in the GenBank database). In addition, only one GenBank entry corresponded to HHV4b (see locus HS4U2IR2).

Sequences encompassing the EBNA2 gene entries were aligned and the gene-coding regions were evaluated for assay development, according to the present invention. Table 1 presents the primers and probes, thus designed using EBNA2, for a screen assay of HHV4. Also see Table 1 for HHV4a and HHV4b amplicons, SEQ ID NOs 54 and 55.

EXAMPLE 6

Analysis of Clinical Samples

An assay of the present invention was performed using DNA extracted from samples from HHV4 infected patients. Dr. Joanne Streib, at National Jewish Hospital and Research Center (Denver, Colo.), kindly provided the HHV4 patient sera. Six sera samples known to be HHV4-positive were analyzed, using the primers and probe for LMP-1 gene of HHV4 described in example 1.

DNA was extracted from the patient sera via the following procedure described below, per CBI protocol DNAREF00015.
1. Thaw 1.5 mL of patient serum rapidly at 37° C.;
2. Transfer 200 μL of thawed serum to a labeled 1.5 mL microcentrifuge tube;
3. Add 25 μL of Qiagen protease and 200 μL buffer AL to the serum, using the Qiagen QIAamp Blood Mini Kit;
4. Incubate at 70° C. for 10 minutes;
5. Add 210 μL ethanol (95%v/v);
6. Centrifuge the above mixture at 6000×g (8000 rpm) for 1 minute, discard pellet, and apply liquid to a QIAamp spin column in a 2 mL collection tube;
7. Discard filtrate and transfer column to a clean 2 ml collection tube;
8. Add 500 μL Qiagen Buffer AW1 to the column and centrifuge the column at 6000×g (8000 rpm) for 1 minute;
9. Discard filtrate and transfer column to a clean 2 ml collection tube;
10. Add 500 μL Qiagen Buffer AW2 to the column and centrifuge the column at maximum speed 15,000×g for 3 minutes;
11. Discard filtrate and place column in a clean, labeled 1.5 mL collection tube;
12. Add 200 μL Qiagen Buffer AE (preheated to 70° C.) to elute DNA from the column; incubate column at room temperature for 1 minute, and then centrifuge at 6000×g (8000 rpm) for 2 minutes;
13. Use the eluted DNA immediately, or store at −20° C.

Assays were performed to amplify and detect LMP-1 gene of HHV4 in duplicate aliquots of each DNA extract; see Table 4 for results. To confirm that the extracted DNA was a suitable template for purposes of the present invention, each extract also was assayed for beta-actin gene. (Applied Biosystems.)

TABLE 4

Assay results for HHV4 DNA extracted from patient samples

| Patient | TaqMan ® $C_T$ Value | Copies of LMP-1 DNA per mL |
|---|---|---|
| 1 | 33.1 | 27,400 |
|   | 35 | 5,200 |
| 2 | 31.3 | 133,600 |
|   | 30.9 | 189,900 |
| 3 | 36.4 | 1,510 |
|   | 37.2 | 0 |
| 4 | 31.5 | 112,000 |
|   | 32.1 | 67,000 |
| 5 | 40 | 0 |
|   | 34.6 | 7,300 |
| 6 | 28.7 | 1,433,000 |
|   | 28.6 | 1,313,000 |

FIG. 2 illustrates that an assay of the present invention, employing the primers and probe designed for HHV4, has the sensitivity needed to measure as few as 10 copies of target DNA. The results also show that the primers and probe designed by the inventive approach detect the presence of HHV4 viral DNA in patient sera.

The level of viral target DNA detected in patient serum is expected to vary depending on the stage of the disease. High levels of viral DNA would characterize situations where patients are actively shedding virus, while patients with a chronic infection or an infection in remission would have low levels of viral DNA. From the data of Table 4, therefore, the inventors concluded that patient 6 was in a more infectious stage than patients 5, 1, and 3. The source of the patient sera, Dr Streib, confirmed this analysis, based on her assessment of clinical symptoms.

EXAMPLE 7

Second Analysis of Clinical Samples

Pursuant to the present invention, sera from patients diagnosed with MS were assayed for HHV4, HHV6, and HHV7, using primer and probe sets shown in Table 1. Dr. Jacquelyn Friedman, at the Rockefeller University (New York City, N.Y.), kindly provided the patient sera. The inventors were informed that the samples had tested negative for HHV6 by a nested PCR-based technique.

DNA from the patient samples was extracted according to the protocol described above. Assay results for duplicates of each sample are shown in Table 5.

TABLE 5

Results of assay of HHV4, HHV6 and HHV7 in DNA extracted from sera of patients diagnosed with MS

|    | HHV4 Copies/mL | Mean HHV6 Copies/mL | Mean HHV7 Copies/mL |
|----|----------------|---------------------|---------------------|
| MM | <10            | 6580                | <350                |
| RP | <10            | 66,300              | <350                |
| VY | <10            | 160,000             | <350                |
| JS | <10            | 33,100              | <350                |
| ES | <10            | 393,000             | <350                |
| KO | <10            | 99,400              | 1350                |
| LR | <10            | 16,800              | 2000                |
| AZ | not assayed    | 515,000             | 1750                |
| JN | not assayed    | 8990                | 1700                |
| AK | not assayed    | 12,000              | 1750                |
| RU | not assayed    | 7930                | 2300                |
| WM | not assayed    | 4420                | 1700                |
| EN | not assayed    | 127,000             | 2150                |
| EL | not assayed    | 37,600              | 1850                |

The assay results in Table 5 reveal that no patient tested positive for HHV4 (detection limit was 10 copies/mL). Some patients (9/14) were positive for HHV7 (detection limit was 350 copies/mL), and all patients tested positive for HHV6 (detection limit was 10 copies/mL). Concentration of HHV6 in the samples ranged from 4000 to 500,000 copies/mL.

IgM assays had previously demonstrated that 18/43 (42%) of the patient samples tested positive for IgM to HHV6 virus, and that seventeen of the samples had been taken in the course of a viral attack or during the progress of infection. Five of seventeen samples from those active patients were positive (30%). Therefore, IgM assays detected active stages of viral infection only 30% of the time (in five samples), as compared to 17 samples detected by the inventive procedure.

EXAMPLE 8

Third Analysis of Clinical Samples

Dr. Dharam Ablahsi of Advanced Biotechnology, Inc. (Rockville, Md.) kindly provided cell lysates of mammalian cultured cells infected with HHV4, HHV5, HHV6a, HHV6b, or HHV7 virus. Dr. Ablashi also provided miscellaneous patient samples, cord blood, serum, and cerebrospinal fluid for assay.

DNA was extracted from each sample, according to the protocol described above. Assays of the invention were performed for HHV4, HHV5, HHV6, HHV6a, HHV6b and HHV7 viruses, using appropriate primers and probe sets (see Table 1).

The assay results, set out in Table 6, show that cells infected with HHV6a strain GS, for example, tested positive for HHV6 and HHV6a, but tested negative for HHV6b. This conforms to expectations, because the primers and probe for the HHV6 screening assay are designed to detect both HHV6a and HHV6b strain variants. Also as expected, HHV GS tested positive in the HHV6a assay. Conversely, all cells infected with HHV Z-29 (an HHV6b variant) tested positive in the HHV6 screen assay and in the HHV6b assay, but tested negative in the HHV6a assay. Thus, the inventive approach was effective in distinguishing between these strain variants.

TABLE 6

Results of assay using cultured cells or viral samples

| Sample | HHV4 | HHV5 | HHV6 | HHV6a | HHV6b | HHV7 |
|--------|------|------|------|-------|-------|------|
|        | (DNA copies per mL) | | | | | |
| Uninfected cells (HSb2; sup't) | 0 | 0 | 0 | 0 | 0 | 0 |
| HSb2/HHV6a | 0 | 0 | 1.80e9 | 9.1e8 | 0 | 0 |
| Sup't/HHV7 | 0 | 0 | 0 | 0 | 0 | 1.3e9 |
| HHV6a (GS) | 0 | 0 | 2.75e6 | 6.49e7 | 0 | 0 |
| HHV6b (Z-29) | 0 | 0 | 5.2e7 | 0 | 3.7e7 | 0 |
| HHV4 (P3HR) | 1.79e9 | 3,667 | 2,667 | 0 | 0 | 0 |
| HHV5 (AD 169) | 20,333 | 4.01e8 | 0 | 0 | 0 | 0 |

Table 7 shows that bodily fluids from patients diagnosed with chronic fatigue syndrome (CFS) tested positive for HHV6 and HHV7 but not for HHV4 or HHV5. The diagnostic utility of the inventive assays is reflected in the fact that the results shown in Table 7 are consistent with results from other studies which seek to establish the association of CFS with HHV6, and the co-incidence of HHV7 infection. See, for example, Ablashi et al., *J. Clin. Virol.* 16: 179-191 (2000). The utility of the assay is also demonstrated by the ability to make such a diagnostic prediction using samples from CSF, peripheral blood monocyte cells (PBMC), plasma, and serum.

TABLE 7

Results of assay using patient samples

| Diagnosis | Fluid | HHV4 | HHV5 | HHV6 | HHV6B | HHV7 |
|-----------|-------|------|------|------|-------|------|
|           |       | (DNA copies per mL) | | | | |
| CFS | Plasma | 0 | 0 | 40,067 | 0 | 31,167 |
| CFS | Plasma | 0 | 0 | 45,033 | 0 | 70,000 |
| GFS | Plasma | 0 | 0 | 38,067 | 0 | 61,867 |
| CFS | Plasma | 0 | 0 | 49,967 | 0 | 82,300 |
| CFS | Plasma | 0 | 18,700 | 64,533 | 0 | 79,400 |

TABLE 7-continued

Results of assay using patient samples

| Diagnosis | Fluid | HHV4 | HHV5 | HHV6 | HHV6B | HHV7 |
|---|---|---|---|---|---|---|
| | | (DNA copies per mL) | | | | |
| Unkn. | CSF | 0 | 0 | 2.08e6 | 0 | 0 |
| Unkn. | CSF | 0 | 0 | 110,676 | 0 | 0 |
| Karposi's sarcoma | Serum | 0 | 0 | 47,800 | 0 | 56,600 |
| Unkn. | PBMC | 0 | 0 | 1.68e6 | 0 | 0 |
| Unkn. | PBMC | 0 | 0 | 83,333 | 0 | 0 |

Table 8 illustrates that the assay of the invention is advantageous compared with methodologies previously employed in the art. Regular reverse transcriptase PCR failed to detect HHV6 in a biological sample from four individuals contained HHV6. The procedure of the invention unambiguously detected HHV6 in three of the four individuals. Accordingly, the assay of the invention improves the ability to detect HHV beyond the capabilities of current technology.

TABLE 8

Assay results, expressed in copies/mL of HHV6, for conventional reverse transcriptase PCR reaction and assay of the invention.

| Patient | Conventional RT PCR assay | Assay of the invention |
|---|---|---|
| 1 | Negative | 44,000 |
| 2 | Negative | 42,450 |
| 3 | Negative | 23,370 |
| 4 | Negative | 0 |

TABLE 1

Primers, probes, and amplicons for assays of individual HHV types

| SEQ ID NO | NAME | LENGTH | SEQUENCE |
|---|---|---|---|
| 1 | HHV1 TK Forward Primer | 20 | GTAATGACAAGCGCCCAGAT |
| 2 | HHV1 TK Reverse Primer | 20 | ATGCTGCCCATAAGGTATCG |
| 3 | HHV1 TK Probe | 20 | CGTTCTGGCTCCTCATATCG |
| 48 | HHV1 TK Amplicon | 188 | |
| 4 | HHV2 TK Forward primer | 19 | CTCCGAGACCCTGACGAAC |
| 5 | HHV2 TK Reverse primer | 20 | GGCGTGCTGATTGTTATCTG |
| 6 | HHV2 TK Probe | 19 | ACACGCAGCACCGTCTGGA |
| 49 | HHV2 TK Amplicon | 114 | |
| 7 | DR HHV2 TK Forward primer | 20 | ATCAGCGTCAGAGCGTTCCC |
| 8 | DR HHV2 TK Reverse primer | 21 | GGACGTAGACGATATTGTCGT |
| 9 | DR HHV2 TK Probe | 24 | GTAGAAGCGGATATGGCTTCTCGC |
| 50 | DR HHV2 TK Amplicon | 327 | |
| 13 | HHV3 TK Forward primer | 20 | GTATTGGCGTAACCTTGCAG |
| 14 | HHV3 TK Reverse Primer | 20 | CATAATTGCATGCGGAGAAC |
| 15 | HHV3 TK Probe | 20 | AGACGCACAACGCCTCACGG |
| 52 | HHV3 TK Amplicon | 148 | |
| 25 | HHV5 IE Forward primer | 24 | TGCAGAGCATGTATGAGAACTACA |
| 26 | HHV5 IE Reverse primer | 20 | CAGCCATTGGTGGTCTTAGG |
| 27 | HHV5 IE Probe | 21 | GAAGCCATCCACATCTCCCGC |
| 56 | HHV5 IE Amplicon | 235 | |
| 42 | HHV7 glyB Forward primer | 21 | GCTGACTTTGTCATGACTGGA |
| 43 | HHV7 glyB Reverse primer | 18 | AGACGCGCAAGAAACCTC |
| 44 | HHV7 glyB Probe | 21 | TGTTCAATTGCCAGCGGGACA |
| 60 | HHV7 Amplicon | 108 | |
| 45 | HHV8 K1 Forward primer | 19 | TCGTSTCGCCTGTCAAATC |
| 46 | HHV8 K1 Reverse primer | 23 | ATCCTTGGTACACACCMTAG |

TABLE 1-continued

Primers, probes, and amplicons for assays of individual HHV types

| SEQ ID NO | NAME | LENGTH | SEQUENCE |
|---|---|---|---|
| 47 | HHV8 K1 Probe | 27 | TTCTTGTATTTATGACRCTCGTAGCTC |
| 61 | HHV8 Amplicon | 226 | |
| 19 | HHV4a EBNA Forward primer | 20 | GTCCAGTCCTCGGTCTTCAT |
| 20 | HHV4a EBNA Reverse primer | 20 | GAGCCTCTGGGCTATTATGG |
| 21 | HHV4a EBNA Probe | 20 | CTCCTGGCCCATCGAATGCC |
| 54 | HHV4a EBNA Ampicon | | |
| 22 | HHV4b EBNA Forward primer | 20 | CCCGTCTGTAGAGTGACACC |
| 23 | HHV4b EBNA Reverse primer | 20 | GCCCTCCCAACTTTCATCTA |
| 24 | HHV4b EBNA Probe | 20 | CCCAGTGATTGGTATCCTCCAACGT |
| 55 | HHV4b EBNA Amplicon | 116 | |
| 36 | HHV6a Forward primer | 22 | GTTGAAGGGACAGAACAAGATG |
| 37 | HHV6a Reverse primer | 20 | GCAGCTGAATCAGAGTTTGC |
| 38 | HHV6a Probe | 34 | CGGCACCCTATGAGAGTGAAAGCG |
| 59 | HHV6a Amplicon | 152 | |
| 39 | HHV6b Forward primer | 21 | AACTCCAAGTGTACCGAAACG |
| 40 | HHV6b Reverse primer | 21 | GGTGCTGAGTGATCAGTTTCA |
| 41 | HHV6b Probe | 26 | TGTGATGGTTTCCATGACAACCCTTT |
| 58 | HHV6b Amplicon | 221 | |

In SEQ ID NOS: 7, 8, 9, and 50, DR = "drug resistant".
Nucleotide degeneracy codes for HHV8 are: C/G = 5; A/C = M; A/G = R

TABLE 2

Probes for screening assays of the invention

| SEQ ID NO | Name | Length | Sequence |
|---|---|---|---|
| 10 | DR HHV(1+2) Forward primer | 20 | AGTTGCTGGCCCCCAACGG C |
| 11 | DR HHV(1 + 2) Reverse primer | 20 | AAACGTGCGCGCCAGGTCGC G |
| 12 | DR HHV(1 + 2) Probe | 20 | TTTATCCTGGATTACGACCA G           T |
| 51 | DR HHV(1 + 2) Amplicon | 205 | |
| 16 | HHV(4a + 4b) LMP-1 Forward primer | 19 | GCACCCTCAACAAGCTACC |
| 17 | HHV(4a + 4b) LMP-1 Reverse primer | 21 | TAGGTTTTGAGAGCAGAGTGG |
| 18 | HHV(4a + 4b) LMP-1 Probe | 24 | CTAACTCCAACGAGGGCAGACACC |
| 53 | HHV(4a + 4b) LMP-1 Amplicon | 121 | |
| 28 | HHV(6a + 6b) IE Forward primer | 23 | GAGAGTGAAGATGAAGAGGATGG |
| 29 | HHV(6a + 6b) IE Reverse primer | 22 | TTATTGGGATGGTAAACACTGG |
| 30 | HHV(6a + 6b) IE Probe 1 | 25 | TCATCTGACTCGCTGCTCGATTCAG |

TABLE 2-continued

Probes for screening assays of the invention

| SEQ ID NO | Name | Length | Sequence |
|---|---|---|---|
| 31 | HHV(6a + 6b) IE Probe 2 | 25 | TCATCTGACTCGCTACTCGATTCAG |
| 32 | HHV(6a + 6b) IE Probe 3 | 25 | TCATTTGACTCGCTGCTCGATTCAG |
| 33 | HHV(6a + 6b) gB Forward primer | 20 | GGGAATTTGGCAGAATCTTG |
| 34 | HHV(6a + 6b) gB Reverse primer | 20 | GACCGTAAACCTGAGACACG |
| 35 | HHV(6a + 6b) gB Probe | 27 | GGAACGATAACGATGTTGCACGAACTT |
| 57 | HHV(6a + 6b) gB Amplicon | 106 | |

What is claimed is:

1. A set of polynucleotide molecules wherein the set comprises the polynucleotide molecules consisting of SEQ ID NOS: 33, 34, and 35 and optionally a fourth polynucleotide molecule comprising SEQ ID NO: 57.

2. A set of polynucleotide molecules according to claim 1, further comprising polynucleotides consisting of SEQ ID NOS: 1, 2 and 3, and optionally a polynucleotide molecule comprising SEQ ID NO: 48.

3. A set of polynucleotide molecules according to claim 1, wherein the set is further comprising polynucleotides consisting of SEQ ID NOS: 4, 5 and 6, and optionally a polynucleotide molecule comprising SEQ ID NO: 49.

4. A set of polynucleotide molecules according to claim 1, further comprising polynucleotides consisting of SEQ ID NOS: 7, 8, and 9, and optionally a polynucleotide molecule comprising SEQ ID NO: 50.

5. A set of polynucleotide molecules according to claim 1, further comprising polynucleotides consisting of SEQ ID NOS: 10, 11 and 12, and optionally a polynucleotide molecule comprising SEQ ID NO: 51.

6. A set of polynucleotide molecules according to claim 1, further comprising polynucleotides consisting of SEQ ID NOS: 13, 14, and 15, and optionally a polynucleotide molecule comprising SEQ ID NO: 52.

7. A set of polynucleotide molecules according to claim 1, further comprising polynucleotides consisting of SEQ ID NOS: 16, 17, and 18, and optionally a polynucleotide molecule comprising SEQ ID NO: 53.

8. A set of polynucleotide molecules according to claim 1, further comprising polynucleotides consisting of SEQ ID NOS: 19, 20, and 21, and optionally a polynucleotide molecule comprising SEQ ID NO: 54.

9. A set of polynucleotide molecules according to claim 1, further comprising polynucleotides consisting of SEQ ID NOS: 22, 23, and 24, and optionally a polynucleotide molecule comprising SEQ ID NO: 55.

10. A set of polynucleotide molecules according to claim 1, further comprising polynucleotides consisting of SEQ ID NOS: 25, 26, and 27, and optionally a polynucleotide molecule comprising SEQ ID NO: 56.

11. A set of polynucleotide molecules according to claim 1, further comprising polynucleotides consisting of SEQ ID NOS: 36, 37, and 38, and optionally a polynucleotide molecule comprising SEQ ID NO: 59.

12. A set of polynucleotide molecules according to claim 1, further comprising polynucleotides consisting of SEQ ID NOS: 39, 40, and 41, and optionally a polynucleotide molecule comprising SEQ ID NO: 58.

13. A set of polynucleotide molecules according to claim 1, further comprising polynucleotides consisting of SEQ ID NOS: 42, 43, and 44, and optionally a polynucleotide molecule comprising SEQ ID NO: 60.

14. A set of polynucleotide molecules according to claim 1, further comprising polynucleotides consisting of SEQ ID NOS: 45, 46, and 47, and optionally a polynucleotide molecule comprising SEQ ID NO: 61.

15. The set of polynucleotide molecules according to claim 1, further comprising polynucleotide molecules consisting of SEQ ID NOS: 16, 17, 18, 25, 26, 27, 42, 43, and 44, and optionally polynucleotide molecules comprising SEQ ID NOS: 43, 56 and 60.

16. A method for detecting infection by HHV6 in a sample from an individual suspected of being infected with HHV6, comprising:

(a) amplifying, in the course of a single amplification reaction, a target segment of an HHV6 glycoprotein B gene comprising SEQ ID NO: 57 using primers and a probe consisting of SEQ ID NOS: 33, 34, and 35 and (b) interpolating the number of HHV6 viral nucleic acid copies in the sample by comparing the number of amplification cycles required for detection of the target segment to the number of amplification cycles required to detect a known quantity of the target segment.

17. A method for detecting infection by either HHV6a or HHV6b in a sample from an individual suspected of being infected with either HHV6a or HHV6b, comprising:

(a) amplifying, in the course of a single amplification reaction, a target segment of an HHV6 glycoprotein B gene comprising SEQ ID NO: 57, using primers and a probe consisting of SEQ ID NOS: 33, 34, and 35; and (b) interpolating the number of either HHV6a or HHV6b viral nucleic acid copies in the sample by comparing the number of amplification cycles required for detection of the target segment to the number of amplification cycles required to detect a known quantity of the target segment.

* * * * *

SEQUENCE LISTING

<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
gcaccctcaa caagctacc                                                  19

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ctaactccaa cgagggcaga cacc                                            24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
taggttttga gagcagagtg g                                               21

<210> SEQ ID NO 4
<211> LENGTH: 121
<212> TYPE: DNA
<213> ORGANISM: Human herpesvirus 4

<400> SEQUENCE: 4
taggttttga gagcagagtg ggggtccgtc gccggctcca ctcacgagca ggtggtgtct     60
gccctcgttg gagttagagt cagattcatg gccagaatca tcggtagctt gttgagggtg    120
c                                                                    121

<210> SEQ ID NO 5
<211> LENGTH: 23

```
<212> TYPE: DNA
<213> ORGANISM: Artificial Sequence
<220> FEATURE:
<223> OTHER INFORMATION: Description of Artificial Sequence: Primer

<400> SEQUENCE: 5
gagagtgaag atgaagagga tgg                                              23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tcatctgact cgctgctcga ttcag                                            25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tcatctgact cgctactcga ttcag                                            25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tcatttgact cgctgctcga ttcag                                            25

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9
ttattgggat ggtaaacact gg                                               22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
gggaatttgg cagaatcttg                                                  20

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 11
cgaacgataa cgatgttgca cgaactt                                                27

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
gaccgtaaac ctcagacacg                                                        20

<210> SEQ ID NO 13
<211> LENGTH: 106
<212> TYPE: DNA
<213> ORGANISM: Human herpesvirus 6

<400> SEQUENCE: 13
gaccgtaaac ctcagacacg atactcgatg gactgatctt actaagttcg tgcaacatcg            60
ttatcgttcg tttttgatcg aggcaccaag attctgccaa attccc                          106

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
tgcagagcat gtatgagaac taca                                                   24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
caagccatcc acatctcccg c                                                      21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
cagccattgg tggtcttagg                                                        20

<210> SEQ ID NO 17
<211> LENGTH: 235
<212> TYPE: DNA
<213> ORGANISM: Human herpesvirus 5

<400> SEQUENCE: 17
cagccattgg tggtcttagg gaaggctgag ttcttggtaa agaactctat attcctgtag            60
cacatataca tcatctttct cctaagttca tccttttag cacgggcctt agcctgcagt            120

-continued

| gcacccccca acttgttagc ggcgcccttg ctcacatcat gcagctcctt aatacaagcc | 180 |
| atccacatct cccgcttatc ctcaggtaca atgtagttct catacatgct ctgca | 235 |

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18

| gctgactttg tcatgactgg a | 21 |

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19

| tgttcaattg ccaccgggac a | 21 |

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 20

| agacgcgcaa gaaacctc | 18 |

<210> SEQ ID NO 21
<211> LENGTH: 108
<212> TYPE: DNA
<213> ORGANISM: Human herpesvirus 7

<400> SEQUENCE: 21

| gctgactttg tcatgactgg acacaatcag catttaccat ttcgaatttg ttcaattgcc | 60 |
| accgggacag atttagtgcg ttttgacagg gaggtttctt gcgcgtct | 108 |

<210> SEQ ID NO 22
<211> LENGTH: 321
<212> TYPE: DNA
<213> ORGANISM: Human herpesvirus 4

<400> SEQUENCE: 22

| caggaaacag ctatgaccat gattacgcca agcttggtac cgagctcgga tccactagta | 60 |
| acggccgcca gtgtgctgga attcggcttt aggttttgag agcagagtgg gggtccgtcg | 120 |
| ccggctccac tcacgagcag gtggtgtctg ccctcgttgg agttagagtc agattcatgg | 180 |
| ccagaatcat cggtagcttg ttgagggtgc aagccgaatt ctgcagatat ccatcacact | 240 |
| ggcggccgct cgagcatgca tctagagggc ccaattcgcc ctatagtgag tcgtattaca | 300 |
| attcactggc cgtcgtttta c | 321 |

<210> SEQ ID NO 23

<400> SEQUENCE: 23

000

-continued

<210> SEQ ID NO 24
<211> LENGTH: 306
<212> TYPE: DNA
<213> ORGANISM: Human herpesvirus 6

<400> SEQUENCE: 24

```
caggaaacag ctatgaccat gattacgcca agcttggtac cgagctcgga tccactagta      60
acggccgcca gtgtgctgga attcggcttg accgtaaacc tcagacacga tactcgatgg     120
actgatctta ctaagttcgt gcaacatcgt tatcgttcgt ttttgatcga ggcaccaaga     180
ttctgccaaa ttcccaagcc gaattctgca gatatccatc acactggcgg ccgctcgagc     240
atgcatctag agggcccaat tcgccctata gtgagtcgta ttacaattca ctggccgtcg     300
ttttac                                                               306
```

<210> SEQ ID NO 25
<211> LENGTH: 435
<212> TYPE: DNA
<213> ORGANISM: Human herpesvirus 5

<400> SEQUENCE: 25

```
caggaaacag ctatgaccat gattacgcca agcttggtac cgagctcgga tccactagta      60
acggccgcca gtgtgctgga attcggcttc agccattggt ggtcttaggg aaggctgagt     120
tcttggtaaa gaactctata ttcctgtagc acatatacat catctttctc ctaagttcat     180
ccttttttagc acgggcctta gcctgcagtg cacccccccaa cttgttagcg gcgcccttgc     240
tcacatcatg cagctcctta atacaagcca tccacatctc ccgcttatcc tcaggtacaa     300
tgtagttctc atacatgctc tgcaaagccg aattctgcag atatccatca cactggcggc     360
cgctcgagca tgcatctaga gggcccaatt cgccctatag tgagtcgtat tacaattcac     420
tggccgtcgt tttac                                                     435
```

<210> SEQ ID NO 26
<211> LENGTH: 308
<212> TYPE: DNA
<213> ORGANISM: Human herpesvirus 7

<400> SEQUENCE: 26

```
caggaaacag ctatgaccat gattacgcca agcttggtac cgagctcgga tccactagta      60
acggccgcca gtgtgctgga attcggcttg ctgactttgt catgactgga cacaatcagc     120
atttaccatt tcgaatttgt tcaattgcca ccgggacaga tttagtgcgt tttgacaggg     180
aggtttcttg cgcgtctaag ccgaattctg cagatatcca tcacactggc ggccgctcga     240
gcatgcatct agagggccca attcgcccta tagtgagtcg tattacaatt cactggccgt     300
cgttttac                                                             308
```